United States Patent [19]

Marzi et al.

[11] Patent Number: 5,272,151

[45] Date of Patent: Dec. 21, 1993

[54] AMINOACYL AND OLIGOPEPTIDYL DERIVATIVES OF ALLOPURINOL EXHIBITING IMMUNOSTIMULATORY ACTIVITY, AND PHARMACEUTICAL FORMULATIONS CONTAINING THESE SUBSTANCES

[75] Inventors: Mauro Marzi; Patrizia Minetti, both of Rome; Piero Foresta, Pomezia; Maria O. Tinti, Rome, all of Italy

[73] Assignee: Sigma-Tau Industrie Farmaceutiche Riunite S.p.A., Rome, Italy

[21] Appl. No.: 854,916

[22] Filed: Mar. 20, 1992

[30] Foreign Application Priority Data

Mar. 22, 1991 [IT] Italy ................ RM91 A 000189

[51] Int. Cl.$^5$ .......................... A61K 31/495
[52] U.S. Cl. .................... 514/258; 544/262; 514/17; 514/18; 514/19; 530/330; 530/331
[58] Field of Search .................. 514/258; 544/262

[56] References Cited

U.S. PATENT DOCUMENTS

| | | | |
|---|---|---|---|
| 3,165,520 | 1/1965 | Schmidt | 544/262 |
| 4,567,182 | 1/1986 | Ferraris | 514/262 |
| 4,602,089 | 7/1986 | Simon | 544/262 |
| 4,663,326 | 5/1987 | Hamilton | 544/262 |
| 4,694,006 | 9/1987 | Bundgaard et al. | 544/262 |

FOREIGN PATENT DOCUMENTS

| | | |
|---|---|---|
| 0077460B1 | 4/1983 | European Pat. Off. |
| WO EP88/01194 | 12/1988 | European Pat. Off. |
| WO85/00368 | 1/1985 | World Int. Prop. O. |

OTHER PUBLICATIONS

Chem. Abstr. vol. 104 Entry 19600h (1986), Abstr. WO85–00368.

Chem. Abstr. vol. 112 Entry 36465a (1990), Abstr WO89–05818.

Chem. Abstr vol. 99 Entry 122919w (1983), Abstr EP 77460.

(List continued on next page.)

Primary Examiner—Donald G. Daus
Attorney, Agent, or Firm—Oblon, Spivak, McClelland, Maier & Neustadt

[57] ABSTRACT

The present invention concerns aminoacyl and oligopeptidyl derivatives of allopurinol (1,5-dihydro-4H-pyrazolo-[3,4-d]-pyrimidin-4-one) of general formula (I), and related salts with

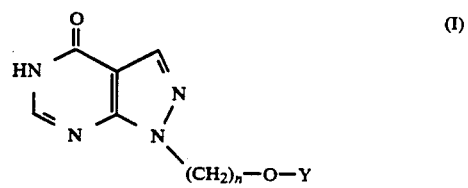

pharmacologically-acceptable cations, in which n is an integer between 2 and 6, preferably 5, Y is H or CO—A, in which A is a racemic or chiral amino acid, dipeptide, tripeptide, tetrapeptide, or pentapeptide chosen, respectively, from the groups consisting of:

a) arginine, aspartic acid, lysine, leucine;
b) glycylaspartate, glycylglycine, aspartylarginine, leucylarginine, alanylglycine;
c) arginyllysylaspartate, aspartyllysylarginine, lysylprolylarginine, prolylprolylarginine, lysylhistidylglycinamide, prolylphenylalanylarginine, phenylalanylprolylarginine;
d) arginyllysylaspartylvaline, valylaspartyllysylarginine, threonylvalylleucylhistidine;
e) arginyllysylaspartylvalyltyrosine.

10 Claims, No Drawings

OTHER PUBLICATIONS

Beauchamp et al., J. Med. Chem. vol. 28 pp. 982–987 (1985).

Kha-Vang-Thaug et al. Chem. Abstr vol. 74 Entry 107635r (1971).

*Hans Bundgaard et al,* "Allopurinol Prodrugs. IV Improved Rectal and Parenteral Delivery of Allopurinol Using the Prodrug Approach as Evaluated in Rabbits," International Journal of Pharmaceutics, vol. 27, (1985), pp. 71–80.

*Kha Vang Thang et al,* "Inhibition De La Xanthine-Oxydase Par l'Allopurinol (1 H–5 H Dihydro–4,5 Pyrazolo [3,4–D] Pyrimidinone–4) (Etude Du Processus D'Oxydation et de L'Effet de l'Aminomethylation)," C.R. Acad. SC. Paris, vol. 272, Jan. 25, 1971, pp. 639–642.

*Roland K. Robins et al,* "Purine Analog Inhibitors of Xanthine Oxidase—Structure Activity Relationship and Proposed Binding of the Molybdenum Cofactor," J. Heterocyclic Chem., vol. 22, (1985), pp. 601–634.

Derwent Abstract of WO89–05818 (1989).

*B. R. Baker et al,* "Irreversible Enzyme Inhibitors. CXXVI. Hydrocarbon Interaction with Xanthine Oxidase by Phenyl Substituents on Purines and Pyrazolo[3,4–D]Pyrimidines," J. Med. Chem., vol. 11, (1968), pp. 661–666.

*R. Stradi et al,* "Synthetic Biological Response Modifiers; Part 1. Synthesis and Immunomodulatory Properties of Some $N^2$-($\omega$-(Hypoxanthin-9-Yl)Alkoxycarbonyl)-L-Arginines," Il Farmaco, vol. 45, (1990), pp. 39–47.

*Luis H. Toledo-Pere Yra et al,* "A Study of the Immunosuppressive Effect of Allopurinol," Immunological Communications, vol. 9(1), (1980), pp. 7–11.

AMINOACYL AND OLIGOPEPTIDYL DERIVATIVES OF ALLOPURINOL EXHIBITING IMMUNOSTIMULATORY ACTIVITY, AND PHARMACEUTICAL FORMULATIONS CONTAINING THESE SUBSTANCES

The present invention concerns aminoacyl and oligopeptidyl derivatives of allopurinol (1,5-dihydro-4H-pyrazolo-[3,4-d]-pyrimidin-4-one) of general formula (I), and related salts with

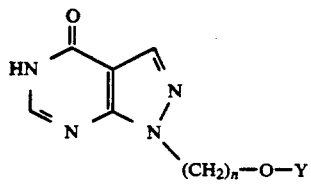

pharmacologically-acceptable cations, in which n is an integer between 2 and 6, preferably 5, Y is H or CO—A, in which A is a racemic or chiral amino acid, dipeptide, tripeptide, tetrapeptide, or pentapeptide chosen, respectively, from the groups consisting of:
a) arginine, aspartic acid, lysine, leucine;
b) glycylaspartate, glycylglycine, aspartylarginine, leucylarginine, alanylglycine;
c) arginyllysylaspartate, aspartyllysylarginine, lysylprolylarginine, prolylprolylarginine, lysylhistidylglycinamide, prolylphenylalanylarginine, phenylalanylprolylarginine;
d) arginyllysylaspartylvaline, valylaspartyllysylarginine, threonylvalylleucylhistidine;
e) arginyllysylaspartylvalyltyrosine.

For the purposes of the present description, "amino acid, dipeptide, tripeptide, tetrapeptide, or pentapeptide" are taken to mean an amino acid, dipeptidyl, tripeptidyl, tetrapeptidyl, or pentapeptidyl moiety bonded to a CO group by an amino nitrogen. By "pharmacologically-acceptable cations" is meant cations such as sodium, potassium, magnesium, ammonium, and whichever other cations experts in the field may elect to designate as pharmacologically acceptable. These oligopeptide derivatives are endowed with immunostimulatory activity and can be compounded into pharmaceutical preparations administrable either parenterally or per os.

To the best knowledge of the applicant, the compounds described herein are most comparable, from pharmacologic and immunostimulatory perspectives, to N-alfa-5-(hypoxanthin-9-yl)-pentyloxycarbonylarginine [see patent EP 0 077 460 and *Il Farmaco*, 45: 39 (1990)].

Other analogous compounds, namely dipeptides and tripeptides of hypoxanthine, in which the oligopeptide portions differ from those of the compounds described in the present invention, are cited in patent application PCT 9/05818. These analogous compounds were not characterised, nor were pharmacological data submitted to support a claim for immunomodulatory activity. Furthermore, in both of the aforementioned patents the purine is hypoxanthine, whilst in the present invention the purine is allopurinol. Allopurinol is known to be an inhibitor of xanthine oxidase [*Heterocyclic Chem.*, 22: 601 (1985); *J. Med. Chem.*, 11: 661 (1968)], and also exhibits anti-hyperuricaemic (*Merck Index*, 11th cd., p. 278) and immunosuppressive [*Immunol. Commun.*, 9: 7 (1980)] activities.

So far as allopurinol derivatives are concerned, those that structurally most closely resemble the compounds in the present invention are the following:

1) acyclovir analogues having the structure

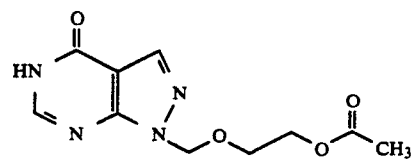

tested as an antiviral agent and found to be inactive [*J. Med. Chem.*, 28: 982 (1985)];

2)

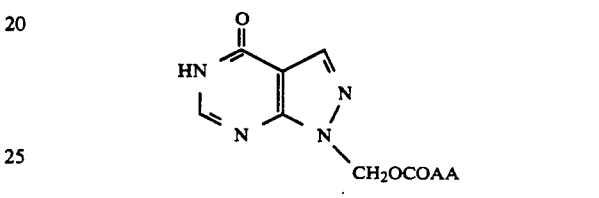

where AA is an amino acid, and claimed as a prodrug of allopurinol [PCT/WO/8500368, *Int. J. Pharm.*, 27: 71 (1985)].

With respect to the state of the art, the applicants considered the compound of patent EP 0 077 460, and found that the compounds of the present invention are more potent immunostimulatory agents in some experiental models than N-alfa-5-(hypoxanthin-9-yl)-pentyloxycarbonylarginine.

The product of general formula (I) for the case where Y is H was prepared as described in Scheme 1 (in which, for simplicity's sake, n was set equal to 5).

Scheme 1

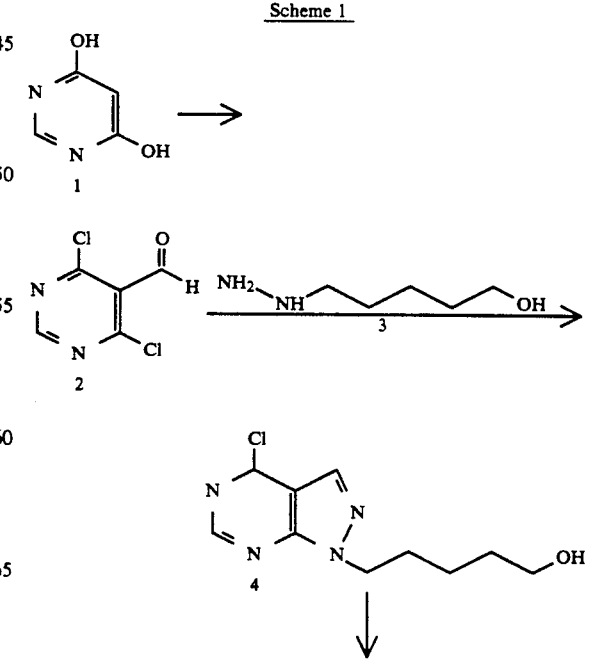

-continued
Scheme 1

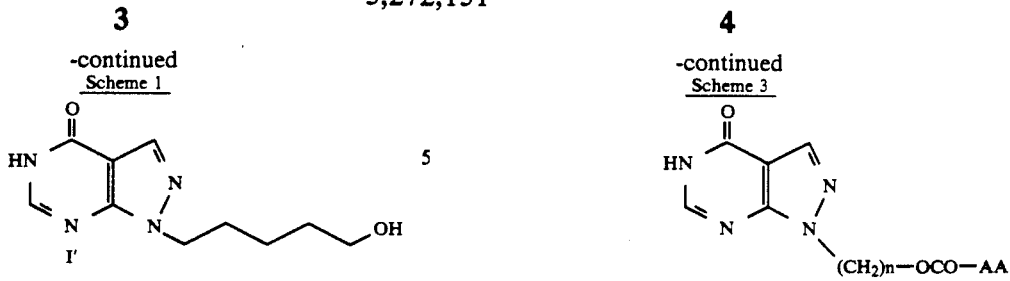

The intermediate H₂N—NH—(CH₂)ₙ—OH was synthesized as described in Scheme 2 (in which, for simplicity's sake, n was set equal to 5).

Scheme 2

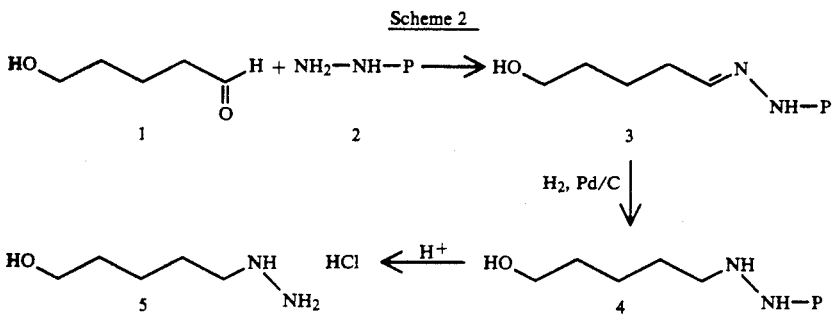

P = protecting group

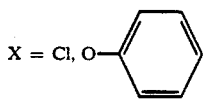

AA = amino acid or peptide

The hydroxyaldehyde was condensed with a hydrazine protected as a t-butoxycarbonyl or carboxy or carboxamide in a solvent such as hexane or toluene at a temperature ranging between 60°-120° C. for a time ranging between 0.5-1.5 h. Upon cooling, the product was precipitated and recovered by filtration. Product 3 was hydrogenated in the presence of a catalyst such as 5-10% Pd/C or PtO₂ in a solvent such as ethanol or water or a water-alcohol mixture, for times ranging from 5 to 24 h, under 2.5 atm of H₂. The protecting group was then removed under acidic conditions, e.g., HCl, to yield N-(hydroxyalkyl)hydrazine chloride.

The products in which Y=CO—A were synthesized as per Scheme 3.

Scheme 3

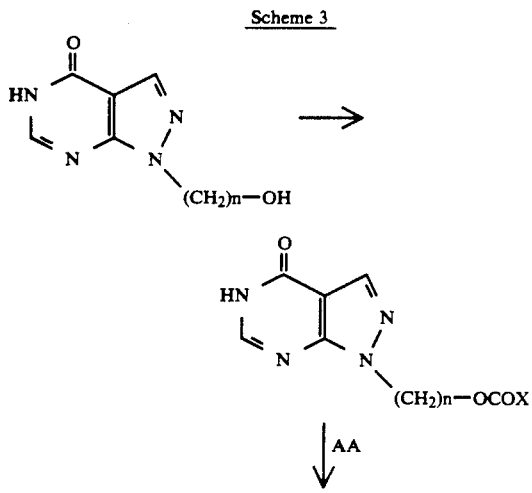

-continued
Scheme 3

(structure I'')

EXAMPLE 1

Preparation of 1,5-dihydro-1-(5-hydroxypentyl)-4-H-pyrazolo-[3,4-d]-pyrimidin-4-one Step a: Preparation of 1-(N-t-butoxycarbonyl)hydrazin-5-hydroxy-1-pentene t-Butylhydrazine (50 g, 0.378 mol) was dissolved in hexane (1.6 L). Technical grade 5-hydroxypentanal (100 g, 0.979 mol) was added, and the solution was refluxed whilst stirring for ca. 30 min. Upon chilling the reaction solution, a white precipitate was obtained, which was recovered by filtration and crystallised from Et₂O.

60 g of the title compound were obtained as white needles.

Yield, 73.4%; R$_f$TLC (EtOAc—McOH, 9:1+0.1 mL NH₃), 0.5; m.p., 90°-91° C.; R$_T$HPLC (μBonapak-NH₂; 50 mM KH₂PO₄—CH₃CN (35:65), pH 5.7; 1 mL/min; 205 nm), 5.71 min; NMR (CDCl₃/DMSO) δ8.9 (1H,s,NH), 7.2 (1H,t,CH=N), 4.1-3.8 (2H,m,CH₂OH), 3.8-3.2 (3H,m,CH₂—C=N,OH), 2.0-1.1 (13H,m+s,CH₂CH₂,CH₃).

Step b: Preparation of 1-(N-t-butoxycarbonyl)hydrazin-5-hydroxypentane

The product from Step a (60 g, 0.277 mol), dissolved in absolute BtOH, was catalytically hydrogenated overnight under 3 atm of H₂ with 10% Pd/C (6 g).

The reaction was terminated by filtering off the catalyst, and the clear solution thus obtained was concentrated in vacuo to give 58 g of a crude product, that was purified on a silica gel column using EtOAc-hexane (7:3) as an eluent. 18 g of an oily, yellowish product were obtained.

Yield, 30%; $R_f$ TLC (EtOAc), 0.43; NMR (CDCl$_3$) δ6.5 (1H,s,NHC), 3.7–3.1 (4H,m,OH,NH—CH$_2$—O), 3.0–2.6 (2H,m,CH$_2$—N), 1.7–1.3 [15H,m+s, CH$_2$CH$_2$CH$_2$,(CH$_3$)$_3$].

Step c: Preparation of 1-hydrazin-5-hydroxypentane chloride

The product of Step b (18 g, 0.082 mol) was dissolved in THF, and gaseous HCl bubbled through the solution until it was saturated. A white gelatinous precipitate formed, which was left stirring overnight.

The reaction mixture was concentrated, and the solid dried in vacuo to give 11.5 g (0.045 mol) of a white, crystalline, highly hygroscopic product.

Yield, 54%; $R_f$TLC (EtOAc—MeOH, 8:2+0.5 mL NH$_3$), 0.24; m.p., 119°–122° C.; NMR (D$_2$O): δ3.7–3.2 (2H,t,CH$_2$—O), 3.1–2.7 (2H,t,CH$_2$—N), 2.0–1.3 (6H,m,CH$_2$CH$_2$CH$_2$).

Step d: Preparation of 4-chloro-1,5-dihydro-1-(5-hydroxypentyl)-4H-pyrazolo-[3,4-d]-pyrimidine 4,6-dichloro-5-formylpyrimidine (3.44 g, 0.019 mol) [prepared as described in *Monats. Chem.*, 96: 1567 (1965)] was dissolved in 70 mL of MeOH and held under a N$_2$ atm for 15 min at −15° C. The product from Step c (3.26 g, 0.021 mol), dissolved in 40 mL of MeOH, was added to the reaction solution, followed by the dropwise addition of triethylamine (5.38 g, 0.053 mol) in 55 mL of MeOH. The reaction mixture was stirred for ca. 20 min at −15° C., then the reaction temperature was raised to 20° C. over a period of about 1 h.

The solvent was removed in vacuo, and the product purified on a silica gel column using CH$_2$Cl$_2$—MeOH (9:1) as an eluent.

Yield, 75%; $R_f$ TLC (CH$_2$Cl$_2$-MeOH, 9.5:0.5), 0.6; NMR (CDCl$_3$): δ8.6 (1H,s,arom), 8.0 (1H,s,arom), 4.4 (2H,t,CH$_2$—O), 3.6 (2H,t,CH$_2$—N), 3.0 (1H,s,OH), 2.1–1.1 (6H,m,CH$_2$CH$_2$CH$_2$).

Step e: Preparation of 1,5-dihydro-1-(5-hydroxypentyl)-4H-pyrazolo-[3,4-d]-pyrimidin-4-one (ST 689)

The product from Step 4 (2.6 g, 0.11 mol) was hydrolysed by refluxing for 1 h with 31.2 mL of 2N NaOH. The reaction was terminated by adjusting the pH of the solution to 7. The solution was concentrated, the resulting solid washed with hot acetone, and the salt removed by filtration. Upon cooling the acetone solution a white crystalline product was obtained, which was recovered by filtration.

Yield, 60%; $R_f$TLC (CH$_2$Cl$_2$-MeOH 9:1), 0.38; m.p. 183°–184° C.; $R_T$ HPLC (μBondapak-NH$_2$; 0.5M KH$_2$PO$_4$—CH$_3$CN, 35:65; 1 mL/min), 3.31 min; NMR (DMSO): δ8.0 (1H,s,arom), 7.95 (1H,s,arom), 6.0 (2H,broad, 20H), 4.2 (2H,t,CH$_2$—O), 3.2 (2H,t,CH$_2$—N), 2.0–1.1 (6H,m,CH$_2$CH$_2$CH$_2$); elem. anal.: calculated (C$_{10}$H$_{14}$N$_4$O$_2$), 54.04% C, 6.35% H, 25.20% N; found, 53.92% C, 6.50% H, 25.35% N.

EXAMPLE 2

Preparation of N-alfa-[5-(1,5-dihydro-4H-pyrazolo-[3,4-d]-pyrimidin-4-on-1-yl)-pentyloxycarbonyl]-L-arginine (ST 816)

Step a: Preparation of 1,5-dihydro-1-(5-pentyloxycarbonyl-phenyl-4H-pyrazolo-[3,4d]-pyrimidin-4-one ST 689 (6.83 g, 0.031 mol) was dissolved in 136 mL of anhydrous pyridine at 0° C., and phenylchloroformate (7.31 g, 0.046 mol) added. The reaction mixture was left to stir overnight at room temperature, then diluted with CH$_2$Cl$_2$ and washed three times with 0.5N HCl and three times with water. The organic phase was dried over anhydrous Na$_2$SO$_4$, filtered, and concentrated to obtain 9.8 g of a crystalline white solid that was purified on a silica gel column using EtOAc-MeOH (9:1) as an eluent.

Yield, 90%; m.p., 172°–174° C.; $R_f$TLC (EtOAc—MeOH, 9:1), 0.8; $R_T$ HPLC (μBondapak-NH$_2$; 0.5M KH$_2$PO$_4$—CH$_3$CN, 35:65; 1 mL/min; 205 nm+R.I.), 2.83; NMR (CDCl$_3$/DMSO): δ11.0 (1H,broad,OH), 7.9 (2H,m,arom), 7.5–6.9 (5H,m,arom), 4.5–3.9 (4H,m,CH$_2$—N,CH$_2$—O), 2.2–1.2 (6H,m, CH$_2$CH$_2$CH$_2$).

Step b: Preparation of N-alfa-[5-(1,5-dihydro-4H-pyrazolo-[3,4-d]-pyrimidin-4-on-1-yl) -pentyloxycarbonyl]-L-nitroarginine The product of Step a (5.3 g, 0.0156 mol) was added to a suspension of N$_{omega}$-nitro-L-arginine (3.42 g, 0.0156 mol) and sodium bicarbonate (1.26 g, 0.015 mol) in 48 mL of DMSO, and the reaction mixture left at 70° C. for 24 h. The reaction mixture was then diluted with EtOAc, and the solid precipitate recovered by filtration. 6 g of a very hygroscopic crude product were obtained.

$R_f$ TLC (EtOAc—MeOH, 6:4), 0.4; NMR (D$_2$O): 8.9–7.5 (4H,broad+s+s,OH, NH,arom), 6.2–4.7 (3H,broad,NH$_2$), 4.1–2.8 (7H,m,CH$_2$—N,CH$_2$—O,-CH—NH,CH$_2$—NH), 2.0–0.9 (10H,m,CH$_2$CH$_2$CH$_2$, CH$_2$CH$_2$).

Step c: Preparation of N-alfa-[5-(1,5-dihydro-4H-pyrazolo-[3,4-d]-pyrimidin-4-on-1-yl-)pentyloxycarbonyl]-L-arginine (ST 816)

The crude product from Step b (1 g, 0.002 mol) was dissolved in 40 mL of MeOH+10 mL of glacial CH$_3$COOH. The mixture was catalytically hydrogenated overnight with 0.1 g of Pd/C under 3 atm of H$_2$. The catalyst was filtered off, and the solvent evaporated to give 600 mg of a very hygroscopic yellowish solid, which was purified on a silica gel column using MeOH as an eluent.

Yield, 70%; m.p., 110° C. (softening); $R_f$ TLC (MeOH), 0.35; $R_T$ HPLC (μBondapak-NH$_2$; 0.05M KH$_2$PO$_4$—CH$_3$CN, 35:65; 1 mL/min; 205 nm+ R.I.), 5.49 min; 300-MHz NMR (DMSO): δ9.5 (1H,broad, COOH), 8.6–7.9 (2H,broad,OH,NH), 8.1 (1H,s,arom), 8,0 (1H,s,arom), 6.3 (1H,m,NH—C) 4.3 (3H,broad,NH,NH$_2$), 4.3 (2H,t,CH$_2$O), 3.9 (2H,m,CH$_2$—N), 3.5 (1H,m, CH—N), 1.8 (2H,m,CH$_2$), 1.7–1.3 (6H,m, CH$_2$CH$_2$CH$_2$), 1.2 (2H,m,CH$_2$); elem. anal.: calculated, 45.95% C, 5.67% H, 25.12% N; found, 45.35% C, 6.11% H, 24.84% N; $[\alpha]_D^{25°}$ C. (c=0.6% H$_2$O), +2.9°.

EXAMPLE 3

Preparation of
N-ε-[5-(1,5-dihydro-4H-pyrazolo-[3,4-d]-pyrimidin-4-on-1-yl)-pentyloxycarbamidino]-L-lysine (ST 817)

The product from Example 2 (2.7 g, 0.0079 mol) was added to 44 mL of DMSO containing $N_{alfa}$-Cbz-L-arginine (3.078 g, 0.0099 mol) and sodium bicarbonate (1.13 g, 0.013 mol). The reaction was left overnight at 70° C., and then ca. 600 mL of EtOAc were added to the reaction flask. After stirring for 2 h, the solid precipitate was recovered by filtration, giving 5.5 g of N-ε-[5-(1,5-dihydro-4H-pyrazolo-[3,4-d]-pyrimidin-4-on-1-yl)-pentyloxycarbamidino]-N-alfa-carbobenzoxy-L-lysine. The crude product was dissolved in 200 ml of MeOH and 60 mL of glacial $CH_3COOH$, and the resulting mixture catalytically hydrogenated overnight with 0.6 g of Pd/C and 3 atm of $H_2$. The catalyst was filtered off, the solvent evaporated, and the resulting solid purified on a silica gel column using MeOH as an eluent.

Yield, 60%; m.p., 130°–140° C. (softening); $R_f$ TLC (MeOH), 0.1; 300-Mz NMR (DMSO): δ8.1 (1H,s,arom), 8.0 (1H,s,arom), 8.0–7.6 (2H,broad,OH, NH—CO), 5.2–4.0 (5H,broad,$NH_2,NH_2$,NH), 4.3 (2H,t,$CH_2O$), 3.8 (2H,m, $CH_2$—N), 3.2 (1H,m,CH—N), 3.1 (2H,t,$CH_2$—O), 1.9–1.2 (10H,m, $CH_2CH_2CH_2,CH_2CH_2$); elem. anal.: conformed to expectations (9–10% water was present); $[\alpha]_D^{25°\,C.}$ (c=0.67% $H_2O$), +1.6°.

EXAMPLE 4

Preparation of
N-alfa-[5-(1,5-dihydro-4H-pyrazolo-[3.4-d]-pyrimidin-4-on-1-yl)-pentyloxycarbonyl]-glycyl-L-aspartic bisodic salt (ST 912)

Step a: Preparation of 1,5-dihydro-1-(5-pentyloxycarbonylchloride)-4H-pyrazolo-[3,4-d]pyrimidin-4-one hydrochloride The product ST 689 (1 g, 0.005 mol) was suspended in 20 ml of anhydrous toluene. 20% phosgene solution in toluene was added dropwise to the suspension (10 ml). After the solution was kept at room temperature under stirring overnight, it was concentrated in vacuo. A white solid was thus obtained. Melting point 127°–132° C., yield 95%.

Step b: Preparation of N-alfa-[5-(1,5-dihydro-4H-pyrazolo-[3,4-d]-pyrimidin-4-on-1-yl)-pentyloxycarbonyl]-glycyl-L-aspartic bisodic salt (ST 912)

$NaHCO_3$(4 g, 0.048 mol) and glycyl-L-aspartic acid (1.6 g, 0.008 mol) were dissolved in 50 ml of $H_2O$. The product from step a was added to the solution portionwise (3 g, 0.01 mol).

The solution was kept at room temperature under stirring overnight, and was subsequently dried and the residue chromatographed on silica, eluant $CH_2Cl_2$—MeOH 1:1. 2.41 g of the product ST 912 were obtained. Yield 50%

$R_f$ TLC: silica, $CHCl_3$—IsoprOH—McOH—$H_2O$—$CH_3COOH$ (42-7-28-10.5-10.5), 0.66; m.p.: 179°–182° C. (soft 170°–179° C.); HPLC: column μBondapack-$NH_2$ (10μ); eluant: $CH_3CN$—$KH_2PO_4$ mM (65-35); flow rate: 1 ml/min; $R_T$: 11.53 min; detector: U.V.; NMR $D_2O$: δ8.1 (s,1H,aromatic); 8.05 (s,1H,arom); 4.45 (m,1H,CH—CO); 4.4 (t,2H,$CH_2$—N); 4.0 (t,2H,$CH_2$—O); 3.81 (s,2H,N—$CH_2$—CO); 2.8–2.4 (m,2H,$CH_2$—COONa); 2.9 (m,2H, $CH_2$); 1.6 (m,2H,$CH_2$); 1.2 (m,2H,$CH_2$); $[\alpha]_D^{25°\,C.}$ = −9.8 (c=1% $H_2O$).

The activity of the compounds of the invention was evaluated using different pharmacologic tests. In some of these tests, N-alfa-5-(hypoxanthin-9-yl)-pentyloxycarbonylarginine (ST 789) was used as a reference compound.

TEST 1

The effects of ST 689 and ST 789 on the production of primary antibodies (Jerne test) in the spleen of mice immunised with sheep red blood cells (SRBC).

Male hybrid $B_6D_2F_1$ mice (Charles River, Italy), 7–8 weeks old, were used in experimental groups of 6 animals each. In this test, each animal was examined individually.

The compounds were administered intraperitoneally at a daily dose of 25 mg/kg from day −3 to day +3, where day 0 was the day of immunisation. The experimental procedure employed is described in Jerne, N. K. et al., *Transpl. Rev.*, 18:30 (1974). Animals were immunised by i.p. administration of a suspension of SRBC ($1 \times 10^8$ cells/mouse in 0.2 mL of PBS buffer). Five days following this treatment, the animals were killed and their spleens sterilely removed. The splenocytes were suspended at a concentration of $1 \times 10^7$ cells/ml, and 0.1 mL of this splenocyte suspension was mixed with 2 mL of warm Hank's agar medium +0.2 mL of 10% SRBC in PBS buffer and incubated in a Petri dish for 60 min at 37° C. (the samples were tested in triplicate). Complement (2 mL of guinea pig serum diluted 1:10 with Tris buffer) was added, and the Petri dishes incubated for 30 min at 37° C. In the presence of complement the cells secreted anti-SRBC antibodies, which evoked a haemolytic reaction. Such a reaction is indicative of lytic plaques in the samples contained in the Petri dishes.

The results are expressed as:

a) number of plaque-forming cells (PFC) in a population of $1 \times 10^6$ cells;

b) number of PFC in intact spleens.

The values obtained were analysed using Dunnett's test (*Biostatistics in Pharmacology*, vol. 2, Pergamon Press) to ascertain the statistical significance of differences between the treated and control animal groups.

As seen in Table 1, ST 689 appeared more active than ST 789 in terms of the number of PFC per spleen, though the increase is not statistically significant with respect to the control.

TABLE 1

Number of plaque-forming cells (PFC) in the spleen of mice immunised with SRBC (day 0) and treated with ST 689 and ST 789 from day −3 through day 3.

| Treatment (25 mg/kg/d i.p.) | PFC/$10^6$ cells (x ± S.E.) | PFC/spleen (x ± S.E.) |
|---|---|---|
| Control | 314 ± 51 | 58680 ± 10484 |
| St 789 | 220 ± 30 | 35011 ± 4761 |
| ST 689 | 303 ± 47 | 64839 ± 15985 |

Dunnett's test = not significant

TEST 2

Evaluation of the protective effects of ST 689 and ST 789 in experimentally-infected immunosuppressed mice.

Male CD1 mice (Charles River, Italy), 6–10 weeks old, were used in experimental groups of 9–20 animals. Systemic infection in the mice was achieved by intrapcritoncal inoculation of a pathogenic species of Klebsiella (*K. oxytoca*), Proteus (*P. mirabilis*), Serratia (*S. marcescens*), and Hscherichia (*E. coli*). Eighteen-hour broth cultures were used to prepare infectious inocula that were either sublethal (Proteus) or which corresponded to an $LD_{30}$ (Serratia) and an $LD_{10}$ (Escherichia, Klebsiella). The bacterial challenge, inoculated i.p. in 0.5 mL of 5% gastric mucin, was designed to cause the death of animals immunodepressed with cyclophosphamide (administered i.p. in 0.2 mL of sterile physiological solution at a dosage of 100 mg/kg) 5 days prior to infection. The compounds were administered i.p. at daily doses of 25 mg/kg from day −5 to day −1 with respect to the day of bacterial inoculation (day 0). The results are expressed as % mortality and were statistically analysed using Fisher's test (*Biostatistics in Pharmacology*, vol. 2, Pergamon Press).

As seen in Table 2, ST 689 exerted a protective activity equal to that of ST 789 in cases of Klebsiella and Proteus infection, and better than ST 789 in the case of Serratia infection.

TABLE 2

Protective effects of ST 689 and ST 789 in immunodepressed mice experimentally infected with four species of Gram-negative pathogens.

| Treatment | % Mortality | | | |
|---|---|---|---|---|
| | *E. coli* | *K. oxytoca* | *S. marcescens* | *P. mirabilis* |
| Control[a] | 1/10(10)% | 1/10(10%) | 6/20(30%) | 0/10(0%) |
| id. con[b] | 8/18(80%) | 6/10(60%) | 16/20(80%) | 6/10(60%) |
| ST 789 (25 mg/kg/d, i.p.) | 2/10(20%)** | 1/10(10%)* | 10/20(50%)* | 1/9(11,1%)* |
| ST 689 (25 mg/kg/d, i.p.) | 4/10(40%) | 1/10(10%)* | 4/20(20%)*** | 1/10(10%)* |

[a]Animals infected with bacteria.
[b]Animals infected after immunosuppression.
[c]Immunodepressed animals treated with the indicated substance at the indicated dosage from day −5 through day −1 relative to the day of bacterial challenge (day 0).
Fisher's test: *p ≦ 0.05; p < 0.02; *p ≦ 0.01

TEST 3

In vitro-ex vivo effects of ST 689 and ST 789 on the chemotactic activity of rat blood granulocytes.

Inbred male Fisher 344 rats (Charles River, Italy), ca. 6 months old, were used in experimental groups of 5 animals. Test animals received the compounds at dosage of 25 mg/kg daily from day −5 through day −1 relative to the day of blood sampling (day 0). The experimental procedure employed is described in Cates, L. K. et al., Modified Boyden chamber method of measuring polymorphonuclear leukocyte chemotaxis, in *Leukocyte chemotaxis*, Raven Press, New York, N.Y., 1978, p. 67.

Blood was sampled from decapitated animals that, after passage through heparinised gauze, was diluted 1/1 with dextran (1.5% in physiological solution) and allowed to sediment for 90 min. The granulocytes, extracted from whole blood by the usual methods; were brought to a concentration of $2 \times 10^6$ cells/mL in Hank's medium. They were then deposited on Millipore filters (3 μm) and placed in migration chambers. These chambers contained either Hank's medium for the evaluation of spontaneous migration, or casein (2 mL of a 5 mg/mL solution) for the evaluation of induced migration. After incubating the samples for 60 min at 37° C. with 5% $CO_2$, the Millipore filters were removed, stained, and inserted between microscope slides. Microscopic observations were performed to determine the furthest distance (in μm) traversed in controls and experimental samples by 2 granulocytes within the rectangular viewing field. Granulocytic migration is expressed as the average value of 10 detailed observations on two filters prepared from each sample.

As seen in Table 3, ST 689 is more active than ST 789 in increasing rat granulocyte chemotaxis.

TABLE 3

Effect in vitro-ex vivo of ST 689[a] and ST 789[a] on spontaneous and casein-induced chemotaxis of rat blood granulocytes.

| Treatment (25 mg/kg /d) | Body wt (g) | Spleen wt (mg) | Chemotaxis (μm ± S.E.) | |
|---|---|---|---|---|
| | | | spontaneous | induced |
| Control | 360.4 ± 5.39 | 608.4 ± 28.37 | 9.60 ± 0.40 | 36.2 ± 1.28 |
| ST 789 | 345.6 ± 8.84 | 610.0 ± 22.00 | 10.01 ± 1.09 | 30.4 ± 2.30 |
| ST 689 | 358.0 ± 9.49 | 591.4 ± 17.13 | 14.40 ± 0.40 | 44.8 ± 1.40 |

[a]The substance was administered i.p. from day −5 through day −1 relative to the day of blood sampling.

TEST 4

Evaluation of the protective effect of ST 689 and ST 789 in tumour-carrying mice, Outbred male CDI mice (Charles River, Italy), 7 weeks old, were used. Experimental groups containing 10 animals were inoculated i.p. with $1 \times 10^4$ Sarcoma 180 cells (ATCC, Rockville, Md., U.S.A.) in 0.1 mL of TC 199 medium. The compounds were administered intraperitoneally in 0.2 mL of sterile physiological solution at daily doses of 25 mg/kg from day +1 through day +10 relative to the day of tumour transplant (day 0). In addition, body weights of the animals were followed from day 0 through day 20. The weights of the animals can be indicative of the development of neoplastic processes. The activity of the compounds was evaluated in terms of % survival expressed as the Mean Survival Time (MST). The data reported in Table 4 indicate a substancial protective effect of ST 689 compared to ST 789 vis-à-vis % survival (20% vs. 10%) in terms of MST (21 vs. 17).

The weights presented in Table 5 in some ways confirm a diminution of neoplastic proliferation in the animals treated with ST 689 compared to those treated with ST 789.

TABLE 4

Protective effects of ST 689[a] and ST 789[a] in mice carrying Sarcome 180.

| Treatment | Died/Total | MST[b] | "U" Mann Whitney Test |
|---|---|---|---|
| Control | 10/10 | 16.0 (15.0–24.0) | |
| ST 789 | 9/10 | 17.0 | NS |

TABLE 4-continued

Protective effects of ST 689$^a$ and ST 789$^a$
in mice carrying Sarcome 180.

| Treatment | Died/Total | MST$^b$ | "U" Mann Whitney Test |
|---|---|---|---|
| (25 mg/kg/d, i.p.) | | (15.75-21.0) | |
| ST 689 | 8/10 | 21.0 | NS |
| (25 mg/kg/d, i.p.) | | (12.0-41.5) | |

NS = not significant
$^a$The substance was administered from day +1 through +10.
$^b$Average survival time calculated from the median and the relative interquartile range.

TABLE 5

Control (x ± S.E.) for Sarcoma 180-carrying animals treated with ST 689 in the manner and at the dosage indicated. The numbers in parentheses correspond to the number of animals still alive on a given day.

| Day | Blank | Control | ST 789 (25 mg/kg/d, i.p.) | ST 689 (25 mg/kg/d, i.p.) |
|---|---|---|---|---|
| 0 | 22.6 ± 0.27 | 21.5 ± 0.73 | 22.8 ± 0.30 | 23.0 ± 0.38 |
| +1 | 23.9 ± 0.30 | 22.2 ± 0.84 | 23.6 ± 0.34 | 23.7 ± 0.34 |
| +3 | 25.1 ± 0.43 | 24.2 ± 0.42 | 24.8 ± 0.30 | 24.5 ± 0.50 |
| +6 | 27.1 ± 0.51 | 27.4 ± 0.54 | 27.6 ± 0.46 | 27.1 ± 0.62 |
| +8 | 27.5 ± 0.56 | 29.1 ± 0.68 | 29.5 ± 0.64 | 28.3 ± 0.97 |
| +10 | 28.9 ± 0.57 | 29.8 ± 0.94 | 31.5 ± 0.92 | 28.4 ± 0.81 |
| +13 | 29.1 ± 0.62 | 31.8 ± 1.00$^{(9)}$ | 32.2 ± 0.96$^{(9)}$ | 28.6 ± 0.89$^{(6)}$ |
| +15 | 30.1 ± 0.69 | 33.0 ± 1.13$^{(7)}$ | 33.4 ± 1.05$^{(8)}$ | 30.5 ± 1.28$^{(6)}$ |
| +17 | 31.4 ± 0.68 | 35.6 ± 1.46$^{(4)}$ | 33.7 ± 1.46$^{(4)}$ | 32.5 ± 1.70$^{(6)}$ |
| +20 | 32.1 ± 0.69 | 35.7 ± 1.92$^{(3)}$ | 34.8 ± 3.90$^{(2)}$ | 32.6 ± 1.85$^{(5)}$ |

TEST 5

In vitro-ex vivo effect of ST 689 and ST 789 on the production of IL-2 by rat splenocytes.

Male Fisher rats (Charles River, Italy), 3 months old, in experimental groups of 5 animals, were treated with the substances at daily dosages of 25 mg/kg from day −5 through day −1 relative to the day the spleens were sampled (day 0). The experimental procedure employed was that reported in [1]. To suspensions of splenocytes, prepared in RPMI 1640 with 10% FCS+1×10$^{-5}$M β-mercaptoethanol and standardised to a concentration of 1×10$^7$ cells/mL, were added equal volumes of ConA at a concentration of 18 μg/mL/well. After incubating for 48 h at 37° C. in the presence of 5% $CO_2$ the samples were centrifuged and the supernates collected. Serial dilutions of the supernates were added to CTLL-2 cells (a line of T-cells requiring IL-2 for growth) standardised at 5×10$^4$ cells/mL. Following an overnight incubation, the samples were labelled with $^3$H—TdR (0.5 μCi/well) for 6 h, then the cells were collected on filters using a cell harvester, and counted (cpm) using a β-counter. The results are expressed in units of IL-2, comparing the counts in the samples to a standard curve prepared with purified IL-2 . . . ls1.

[1] Shalaby, M. R. and Palladino, M. A., Manual of clinical laboratory immunology. American Society for Microbiology, Washington, D.C., 1986, p. 300.

The results reported in Table 6 are indicative of an increase in the production of IL-2 by splenocytes of animals treated with ST 689 compared to those treated with the same dosage of ST 789.

TABLE 6

In vitro-ex vivo effects of ST 689$^a$ and ST 789$^a$ on the appearance of IL-2 in supernates from rat splenocytes.

| Treatment | Weight Survey | | IL-2(U/mL) |
|---|---|---|---|
| | Body weight (g) | Spleen weight (mg) | |
| Control | 283.0 ± 3.40 | 573.6 ± 14.14 | 124.22 ± 14.28 |
| ST 789 | 275.0 ± 3.76 | 539.2 ± 12.11 | 98.43 ± 4.47 |
| ST 689 | 271.6 ± 4.76 | 511.0 ± 22.35 | 183.25 ± 22.55 |

$^a$The substance was administered i.p. at a daily dosage of 25 mg/kg from day −5 through day −1 relative to the day of spleen sampling (day 0).

TEST 6

In vitro-ex vivo effects of ST 689 and ST 789 on phagocytic activity of mouse peritoneal exudate cells (PECs).

Male B$_6$D$_2$F$_1$ mice (Charles River, Italy), 6 weeks old, in experimental groups of 5 animals, were treated with the above substances i.p. at daily doses of 25 mg/kg from day −5 through day −1 relative to the day the PECs were sampled (day 0). The experimental procedure followed those described in [1] and [2]; briefly, the animals in each group were asphyxiated with $CO_2$, the peritoneal cavities repeatedly washed, and the PECs recovered from each experimental group pooled and standardised to 4×10$^6$ cells/mL. Aliquots (250 μL) of phagocyte suspension were added to equal volumes of 0.4% SRBC that had been appropriately opsonised with hyperimmune serum. The samples, prepared in duplicate, were incubated for 1 h and then osmotically shocked to eliminate non-phagocytosed erythrocytes. After adjusting the osmolarity to normal values, the phagocytes were centrifuged and differentially stained. Microscopic counts of cells with phagocytic capabilities and of phagocytosed SRBC in fields of 200 cells were performed in triplicate. The results are expressed as % phagocytic cells, the average number of SRBC phagocytosed per phagocyte, and the total number of SRBC phagocytosed per 100 phagocytes.

[1] Herscowitz, H. B., Manual of macrophage methodology. Marcel Dekker, New York, 1981.
[2] Williams, C. A. and Chase, M. W., Methods in immunology and immunochemistry, vol. 5, Academic Press, Inc., New York, 1976, p. 261.

The results presented in Table 7 show that substance ST 689 exerts an extremely positive effect on the phagocytic capabilities of PECs, all phagocytic parameters having higher values after treatment with ST 689 than after treatment with ST 789.

TABLE 7

In vitro-ex vivo effects of ST 689[a] and ST 789[a] on the phagocytic activities of mouse PECs.

| Treatment | % Phagocylic cells[b] | SRBC phagocytosed[c] | SRBC per phagocyte[d] |
|---|---|---|---|
| Control | 28.0 ± 3.0 | 92.0 ± 7.0 | 3.30 ± 0.10 |
| ST 789 | 31.5 ± 0.5 | 152.5 ± 9.5 | 4.85 ± 0.25 |
| ST 689 | 42.5 ± 0.5 | 229.5 ± 34.5 | 5.40 ± 0.90 |

[a]The substance was administered i.p. at daily dosage of 25 mg/kg from day −5 through day −1 relative to the day of sampling of PECs (day 0).
[b]% of cells that had phagocytosed relative to the number of potential phagocytes present in the PECs.
[c]Average number of SRBC phagocytosed by 100 potential phagocytes.
[d]Average number of SRBC phagocytosed per potential phagocyte.

TEST 7

In vitro-ex vivo effects of substances ST 689 and ST 789 on the cytostatic activity of mouse peritoneal macrophages (MO) towards tumour targets.

Male $B_6D_2F_1$ mice (Charles River, Italy), 7 weeks old, 5 animals per experimental group, were treated with the above substances i.p. at daily dosages of 25 mg/kg from day −5 through day −1 relative to the day of macrophage sampling (day 0). The tumour target, CEM—CM3 human leukaemic lymphoblasts, was admixed with adherent Mo so as to have two different precisely-measured effector:target ratios, viz. 10:1 and 20:1. Each sample, prepared in triplicate in flat-bottom microliter wells, was labelled with $^3H$—TdR (0.05 μCi) by incubation for 18 h at 37° C. The tumour cells from each well were collected on filters, counted in a β-counter, and the % inhibition of tumour target growth determined using the formula.

$$\% \text{ cytostasis} = 1 - \frac{\text{cpm of sample}}{\text{total cpm incorrporated}} \times 100\%$$

The data presented in Table 8 shows that substrate ST 789 produced a definite increase in growth inhibition of the CEM—CM3 cell line, surpassing even the good results obtained with ST 789.

TABLE 8

In vitro-ex vivo effects of ST 689[a] and ST 789[a] on the cytostatic activity of mouse peritoneal Mo challenged with the tumour line CEM-CM3.

| Treatment | % Growth Inhibition 10:1[*] | 20:1[*] |
|---|---|---|
| Control | 1.77 ± 0.18 | 8.37 ± 5.22 |
| ST 789 | 15.85 ± 3.33 | 30.31 ± 5.19 |
| ST 689 | 32.84 ± 1.84 | 47.98 ± 5.46 |

[a]The substance was administered at a daily dosage of 25 mg/kg from day −5 through day −1 relative to the day of Mo sampling (day 0).
[*]effector:target ratio

We claim:

1. An allopurinol of the formula:

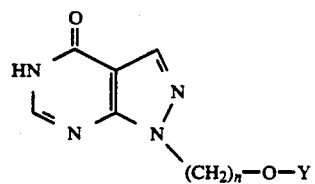

and pharmacologically acceptable salts thereof, wherein Y is H and n is 5.

2. An aminoacyl allopurinol of the formula:

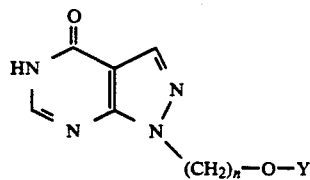

and pharmacologically acceptable salts thereof, wherein Y is CO—A and n is an integer of from 2 to 6, A being a member of the group consisting of arginine, aspartic acid, lysine and leucine, said member being bound to said CO of said Y by an amino nitrogen.

3. The aminoacyl allopurinol of claim 2, wherein n=5.

4. N-alpha-[5-(1,5-dihydro-4H-pyrazolo-[3,4-d]-pyrimidin-4-on-1-yl)pentyloxycarbonyl]-argininc and its salts with pharmacologically-acceptable cations.

5. N-ε-[5-(1,5-dihydro-4H-pyrazolo-[3,4-d]-pyrimidin-4-on-1-yl)pentyloxycarbamidino]-lysine and its salts with pharmacologically-acceptable cations.

6. An oligopeptidyl allopurinol of the formula:

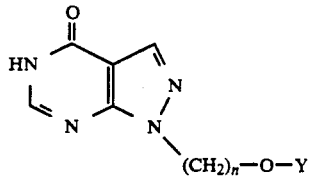

and pharmacologically acceptable salts thereof, wherein Y is CO—A and n is an integer of from 2 to 6, A being glycylaspartate.

7. A composition, comprising an amount of the allopurinol of claim 1 sufficient to exert an immunostimulatory effect on a patient in need thereof, in a pharmaceutically acceptable excipient.

8. The composition of claim 7, wherein said amount of said allopurinol is from about 20 mg to about 100 mg.

9. A composition, comprising an amount of the aminoacyl allopurinol of claim 2 sufficient to exert an immunostimulatory effect on a patient in need thereof, in a pharmaceutically acceptable excipient.

10. The composition of claim 9, wherein said amount of said allopurinol is from about 20 mg to about 100 mg.

* * * * *